US011672405B2

(12) United States Patent
Heni et al.

(10) Patent No.: US 11,672,405 B2
(45) Date of Patent: Jun. 13, 2023

(54) VIDEO ENDOSCOPE AND HANDLE, INCLUDING DRIVEN ROTATION LIMITATION, FOR VIDEO ENDOSCOPE

(71) Applicant: KARL STORZ SE & Co KG, Tuttlingen (DE)

(72) Inventors: Pascal Heni, Tuttlingen (DE); Markus Kupferschmid, Tuttlingen (DE); Jonas Forster, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 80 days.

(21) Appl. No.: 16/906,978

(22) Filed: Jun. 19, 2020

(65) Prior Publication Data

US 2021/0007584 A1 Jan. 14, 2021

(30) Foreign Application Priority Data

Jun. 22, 2019 (DE) .......................... 102019004433.9

(51) Int. Cl.
*A61B 1/00* (2006.01)
*G02B 23/24* (2006.01)
(Continued)

(52) U.S. Cl.
CPC ...... *A61B 1/00066* (2013.01); *A61B 1/00009* (2013.01); *A61B 1/00018* (2013.01);
(Continued)

(58) Field of Classification Search
CPC .......... A61B 2090/035; A61B 1/00066; A61B 1/00124
See application file for complete search history.

(56) References Cited

U.S. PATENT DOCUMENTS 5,988,171 A * 11/1999 Sohn .................. A61B 17/8891
606/232
6,030,339 A 2/2000 Tatsuno et al.
(Continued)

FOREIGN PATENT DOCUMENTS

DE 19925323 A1 12/2000
DE 102007026234 A1 12/2008
(Continued)

OTHER PUBLICATIONS

Neumeyr, T., European Search Report, Ap. EP 20181483, dated Oct. 30, 2020, pp. 1-6, Munich.

*Primary Examiner* — John P Leubecker
*Assistant Examiner* — Minqiao Huang
(74) *Attorney, Agent, or Firm* — David N. Villalpando

(57) ABSTRACT

The invention concerns a handle for a video endoscope including a housing and an interface portion rotatably supported relative to the housing where the interface portion includes a first connector element at its distal end section that is connectable to a second connector element of an associated elongate shaft of the video endoscope. Thereby a detachable, rotatable electrical and/or mechanical connection between the handle and the associated shaft is achieved. The coupling includes an electrical connection assembly arranged at an exterior of the interface portion forming an electrical connection to a stationary electric component of the handle. The handle includes a mechanical rotation stop for a rotation of the interface portion relative to the housing such that a rotation range is limited and damage to the electrical connection assembly is prevented.

10 Claims, 6 Drawing Sheets

(51) Int. Cl.
*H04N 23/50* (2023.01)
*A61B 90/00* (2016.01)
*A61B 1/05* (2006.01)
*A61B 1/06* (2006.01)
*H01R 39/64* (2006.01)
*H04N 23/54* (2023.01)

(52) U.S. Cl.
CPC ...... *A61B 1/00027* (2013.01); *A61B 1/00124* (2013.01); *A61B 1/05* (2013.01); *A61B 1/053* (2013.01); *A61B 1/0661* (2013.01); *A61B 1/0669* (2013.01); *A61B 1/0684* (2013.01); *A61B 90/03* (2016.02); *G02B 23/2484* (2013.01); *H01R 39/643* (2013.01); *H04N 23/54* (2023.01); *A61B 2090/035* (2016.02); *H01R 2201/12* (2013.01); *H04N 23/555* (2023.01)

(56) References Cited

U.S. PATENT DOCUMENTS

| | | | |
|---|---|---|---|
| 6,095,970 | A | 8/2000 | Hidaka et al. |
| 6,346,076 | B1 * | 2/2002 | Rovegno ............ A61B 1/00177 |
| | | | 600/137 |
| 6,692,431 | B2 * | 2/2004 | Kazakevich ............ A61B 1/07 |
| | | | 600/137 |
| 7,212,737 | B2 | 5/2007 | Dehmel et al. |
| 7,241,263 | B2 | 7/2007 | Boulais |
| 7,828,720 | B2 | 11/2010 | Miller et al. |
| 8,187,171 | B2 | 5/2012 | Irion et al. |
| 8,197,400 | B2 | 6/2012 | Boutillette et al. |
| 8,992,424 | B2 | 3/2015 | Orbay et al. |
| 9,107,573 | B2 | 8/2015 | Bimkrant |
| 9,907,457 | B2 | 3/2018 | Grant et al. |
| 2003/0229287 | A1 * | 12/2003 | Flesch .................. A61B 8/4461 |
| | | | 600/466 |
| 2006/0058581 | A1 | 3/2006 | Hanke |
| 2008/0300456 | A1 | 12/2008 | Irion et al. |
| 2010/0125166 | A1 | 5/2010 | Henzler |
| 2011/0193948 | A1 | 8/2011 | Amling et al. |
| 2011/0306834 | A1 | 12/2011 | Schrader et al. |
| 2014/0012130 | A1 * | 1/2014 | Jacobsen ............. H05K 1/0298 |
| | | | 600/424 |
| 2014/0221749 | A1 * | 8/2014 | Grant ................ A61B 1/00096 |
| | | | 600/109 |
| 2014/0276720 | A1 * | 9/2014 | Parihar ............ A61B 17/07207 |
| | | | 606/130 |
| 2014/0357952 | A1 | 12/2014 | Krohn et al. |
| 2015/0085093 | A1 | 3/2015 | Heni et al. |
| 2015/0105620 | A1 | 4/2015 | Oginski et al. |
| 2015/0271370 | A1 * | 9/2015 | Henley ................. A61B 1/051 |
| | | | 348/76 |
| 2017/0209024 | A1 | 7/2017 | Weitzner et al. |
| 2018/0317921 | A1 * | 11/2018 | Cabrera ............ A61B 17/0682 |
| 2019/0125384 | A1 * | 5/2019 | Scheib .................. A61B 17/29 |
| 2019/0282244 | A1 * | 9/2019 | Muse ....................... A61C 3/02 |

FOREIGN PATENT DOCUMENTS

| | | |
|---|---|---|
| DE | 102012206412 A1 | 10/2013 |
| DE | 102017119691 A1 | 2/2019 |
| EP | 1423042 B1 | 9/2012 |
| EP | 3197146 A1 | 7/2017 |
| WO | 00/57770 A2 | 10/2000 |
| WO | 2011143269 A1 | 11/2011 |

* cited by examiner

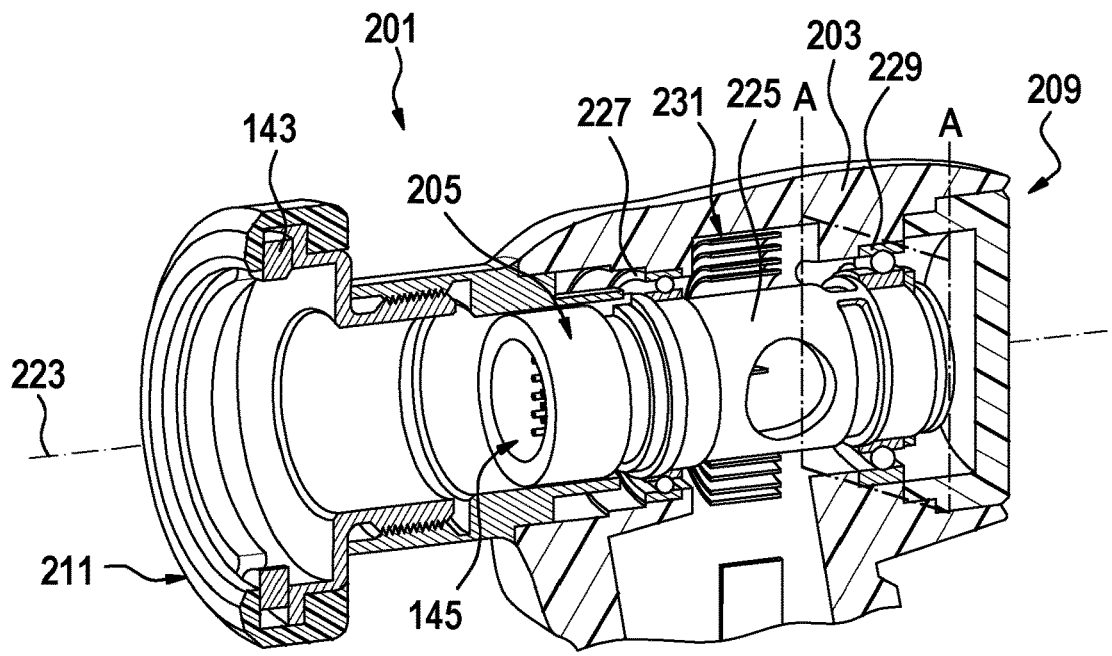
Fig. 9
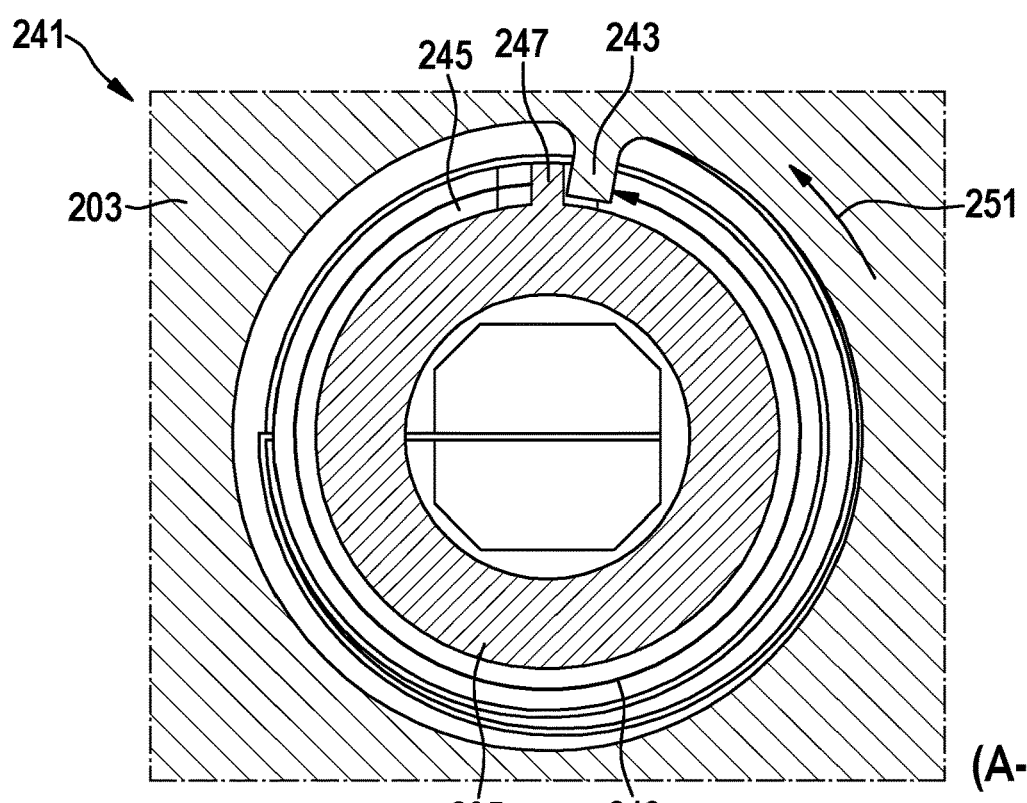
(A-A) Fig. 10

VIDEO ENDOSCOPE AND HANDLE, INCLUDING DRIVEN ROTATION LIMITATION, FOR VIDEO ENDOSCOPE

CROSS REFERENCE TO RELATED APPLICATIONS

This application claims priority to German Patent Application No. 102019004433.9, filed Jun. 22, 2019, and entitled, "Video endoscope and handle for a video endoscope," and is incorporated herein by reference.

FIELD OF THE INVENTION

The invention relates to a handle for a video endoscope, in particular for a medical or industrial video endoscope.

BACKGROUND OF THE INVENTION

For medical or non-medical applications, endoscopes comprise an elongate shaft configured for being introduced into an internal cavity of a human or animal body or another object for examination. For generating an image of an object field in the cavity, an imaging optic is located in a distal (meaning distant from a user) end section of the shaft. On the opposite, proximal (meaning close to the user) end section of the shaft, a handle is attached for operating the endoscope by the user. In case of video endoscopes, which are also known as electronic endoscopes, the generated endoscopic image is picked up by an electronic image sensor, whereby, in a wide-spread design, the electronic image sensor together with the imaging optics are contained in an optic shaft arranged inside the shaft of the video endoscope. Consequently, the image signals generated by the image sensor are transmitted electronically through the shaft and the handle towards the proximal end of the video endoscope and outwards for displaying the endoscopic image on a monitor.

Common video endoscopes are complete systems, wherein the shaft and the handle are permanently fixed to each other. As a complete system, the whole video endoscope must be cleaned and sterilized (generally in an autoclave) after each use. Furthermore during an endoscopic procedure, the user is frequently required to change a rotational orientation of the endoscope in order to vary the view of the object field, and in with the limitations of conventional video endoscopes, the complete video endoscope must be rotated during examination of the cavity. As such, the operator controls, buttons or touch keys, which are usually arranged at the top side of the handle in its upright position, are arranged in an unfavorable position for the user during rotation. This design is especially disadvantageous, because normally the handle is held by the same hand of the user that likewise operates the operator buttons or touch keys.

In order to improve user convenience and provide for ergonomic operation, the shaft of a video endoscope can be designed to be rotatable relative to the handle. The electrical connection between the two relatively rotatable parts, the shaft and the housing of a handle, presents a challenge that can be partially solved by employing a flexible electric connection, for example a flexible ribbon cable. Nevertheless, still, the problem remains that this flexible electric connection may twist around itself, be over extended, or even be damaged and may tear off during rotation of the shaft relatively to the outer housing while using the video endoscope.

In EP 3 197 146 A1, a medical observation device is disclosed that comprises an imaging optical system, an image sensor and an element holding frame with a plurality of optical elements, wherein the element holding frame is capable of being rotated around a rotation shaft with an axial direction orthogonal to the optical axis, wherein the element holding frame is rotatable such that at least one of the optical elements is positioned on an optical axis. The rotation of the element holding frame can be limited by a mechanical stop consisting of a stopper screw, a sliding ring and a workpart including a slide groove. However, EP 3 197 146 A1 does not address the rotation of a shaft of a video endoscope and a rotatable, couplable electric connection.

BRIEF DESCRIPTION OF THE INVENTION

The present invention solves problems faced by the prior art with a new videoendoscopic system comprising a handle for a video endoscope, in particular for a medical or industrial video endoscope, comprising a housing and an interface portion rotatably supported relative to the housing, wherein the interface portion comprises a first connector element at its distal end section, the first connector element is connectable to a second connector element of an associated elongate shaft to form a detachable, rotatable electrical and/or mechanical connection between the handle and the associated shaft, and comprising an electrical connection assembly arranged at an exterior of the interface portion forming an electrical connection to a stationary electric and/or electronic component of the handle, wherein the first connector element is electrically connected to the electrical connection assembly, and the handle comprises a mechanical rotation stop for a rotation of the interface portion relative to the housing, such that a rotation range of the interface portion and/or the connected shaft is limited and damage to the electrical connection assembly is prevented.

Therewith, a handle for a video endo scope is provided which permits the improved handling and orientation of a video endoscope for a user with two separate systems rotatable relative to each other. The shaft may be rotated by the user during use relative to the housing of the handle without reaching the maximum rotational angle allowed by the electrical connection assembly, and therewith there is no danger of damages to the electrical connection assembly or the disconnection of the electrical connectors within the handle as a result of rotation. In addition, of course, at the choice of the operator, the handle may be rotated relative to the stationary shaft, for example for changing the hand position of the operator at a same object view, or the two may be rotated independently, relative to each other. It is particularly beneficial that a rotatable electrical and/or mechanical connection between the shaft and the handle is provided which limits to the rotation of the interface portion and therewith, a connected shaft, to avoid damage to the electrical connection and/or the electrical connection assembly, but still provides operational benefits, such as the ability to maintain a constant orientation of the outer housing of the handle and therefore a constant orientation of the operator controls and keys located on the handle for the user. During an endoscopic operation, the user is generally accustomed to change the direction of rotation of the shaft at any moment during navigation and viewing inside a body cavity, and therefore, the mechanical rotation stop to limit rotation of the interface portion and therewith the connected shaft, improves the electrical reliability of the handle and shaft, and therefore video endoscope is enhanced, permitting the prolongation of an endoscopic procedure and reducing the risk involved in a medical endoscopic intervention.

Thus, an efficient, user-friendly, and electrically reliable handle for a video endoscope is provided to house the image sensor in the distal end of the shaft of the video endoscope in a manner similar to traditional endoscopes wherein a proximal image sensor is housed within a camera head attached to the endoscopic shaft, while enabling an electrical, rather than optical image transmission, from the connected shaft to the handle and, in particular, further to a processing unit.

In addition to allowing a reliable rotation of the shaft relative to the instrument handle to which it maintains an electronic connection, based on the rotatable coupling point comprising the second connector element of the shaft and the first connector element of the interface portion of the handle, a modular video endoscope is presented, free from a permanent fixed connection between the shaft and the handle. Instead a detachable, electrically reliable connection is enabled allowing flexibility in the shaft and handle selection. Consequently, the modular handle is connectable to distinct shafts each with differing properties, such as bore diameter or optical properties, or the same kind of shaft in between individual medical interventions, or during one intervention. Consequently, the shaft is separately cleanable, autoclavable and/or exchangeable without similar treatment of the handle, as the latter normally does not come in contact with body fluids and is not inserted into the cavity, so that the same degree of cleaning, disinfection and/or sterilization procedure is not necessary for the handle as for the shaft.

It is especially beneficial that the mechanical rotation stop is arranged between the interface portion, to which the shaft is connectable via its second connector element to the first connector element of the interface portion, and the housing of the handle, so that the mechanical rotation stop is an inherent property of the handle and not the connectable shaft. Consequently, a more generalized and simpler design of the shaft is enabled. The shafts may, therefore, be designed to be particularly simple to clean and sterilize, as the more complicated mechanism allowing for the shaft's rotation is contained in the detachable handle. Another benefit of the flexible connectability of the shaft to the handle is that, also the shaft can be designed to be disposable, while the handle may be reused. This configuration permits the optimization of expense relating to disposable elements by including more costly, but required, elements to be housed in the reusable handle, while the shafts may include only the elements necessary for their own function.

Overall, a higher versatility is offered to the user by the exchangeability of the shaft to the modular handle as well as from the reliable, distinct rotation of the shaft depending on the object field at the preferred hand movement of the user are enabled. Furthermore, a reliable electrical connection under all possible rotational positions in a predefined rotation range is provided, wherein a bidirectional transmission of electronic power and data from and to an image sensor arranged at the distal end of the shaft to the handle is enabled, allowing collected image data to be transmitted to the handle as well as control data and electric power are transmitted from the handle to the shaft. Power transmitted to the distal end is used to power the image sensor and related circuitry, but may also be used to drive illumination means, such as distally placed light emitting diodes (LED) in certain embodiments.

Due to the rotation limit between the interface portion and the housing of the handle, the shaft connected to the interface portion of the handle is only rotatable to a certain, given angle and/or rotation range, by which a mechanical and electrical safe connection is maintained between the shaft and the interface portion and therewith between the first connector element of the interface portion and the electrical connection assembly arranged at an exterior of the interface portion and furthermore to the stationary electric and/or electronic component of the handle. As the electrical coupling point between the second connector element of the shaft and the first connector element of the interface housing is rotatably supported via the interface housing and connected to the, preferably flexible, electrical connection assembly, arranged at or around the exterior of the interface portion, it is possible to realize the relative rotation between the shaft and the housing of the handle limited by the mechanical stop in each possible rotational direction. Consequently, the rotatable electrical coupling point of the second connector element and the first connector element, which, in principle, would allow an angular rotation of more than 360°, and therefore would introduce a winding of the electrical connection assembly, is respectively limited by the mechanical rotation stop in the handle. Therefore, in embodiments where the electrical connection assembly comprises a coupling spool, with the electrical connection means wound around the outer surface of the interface portion, the coupling spool can be securely driven by the rotation of the interface housing.

One of the primary elements of the invention includes a mechanical rotation stop for a connectable shaft located between the interface portion and the housing of the handle, allowing a rotation, relative to the housing, of the interface portion and, therewith, a shaft connectable to the interface portion, without limiting the rotation of the shaft itself and enabling a reliable electrical connection at the coupling point between the shaft and the interface portion of the housing as well a reliable electrical connection between the coupling point, via an electrical connection assembly around the exterior of the interface portion, to a stationary electrical component of the handle. Hereby, it is particularly beneficial that the mechanical rotation stop is located in the handle and simultaneously and specifically limits the rotation of the endoscopic shaft itself.

As utilized in accordance with the present disclosure, the following terms, unless otherwise indicated, shall be understood to have the following meaning.

In particular, a "video endoscope" (also denominated simply "endoscope") is an endoscope with digital image acquisition and transmission to the proximal end. The video endoscope comprises a shaft and a handle, which are connectable to each other. At least one digital image sensor is located at the distal end section of the elongated shaft for image acquisition. A "video endoscope" is any kind of digital endoscope, for example a mediastinoscope, but may include non-medical scopes used for industrial purposes, often called borescopes.

A "handle" is, in particular, an object that can be moved and/or used by hand, giving the user the ability to exploit the connected tool and/or instrument for its function. A handle is an element of a video endoscope. In particular, the handle comprises a housing and an interface portion which is mounted rotatably via at least one bearing, preferably two bearings, relative to the housing. In particular, the handle is modular in that it can be connected to different shafts with different properties to provide a specific video endoscope combination. The handle enables the user to hold and/or operate and manipulate the connectable shaft and therefore the video endoscope. The handle may comprise a grip or grip portion to facilitate holding the handle by the user. Preferably, at its outer surface, for example on the top face or a side face, the handle comprises one or more control elements, such as buttons or touch keys, for controlling various functions of the endoscope. Preferentially, the control elements are arranged and/or located in such a manner on and/or in the surface of the handle so that the user can operate the control elements with one or more fingers of the same hand which is holding the handle.

The "interface portion" is a separate part of the handle which is rotatably mounted relative to the housing of the handle. The interface portion has an exterior, which may be an outer surface of a body of the interface portion. In particular, the exterior of the interface portion may be formed by an outer surface of the interface portion in such a way that a proximally rotational symmetry with respect to the rotational axis exists. The exterior consists of or comprise a continuous face or may be discontinuous, for example having a grid surface. The interface portion might be formed from solid material. The interface portion may comprise an interior hollow space for including an electric transmission element or other parts. For example, the interface portion can be formed as a hollow cylinder with one face side or both face sides closed. Preferably, at the distal end and/or at and/or inside the distal end section of the interface portion, the first connector element is arranged.

The interface portion is preferably supported rotatably by at least one bearing in the housing. The bearing may provide free rotation of the interface portion around its rotational axis and/or the rotational axis of the bearing. In particular, the bearing is a rotary bearing which holds and supports the interface portion at and/or in the housing. The bearing is, for example, a rolling element bearing, such as a ball bearing, or a plain bearing.

The "elongated shaft" is in particular a rigid tube, and therefore, the video endoscope may be a rigid endoscope, or, as well, the shaft may be formed by a flexible tube and therefore, a flexible video endoscope is provided. In particular, the shaft is configured for being inserted into a cavity to be viewed endoscopically, for example of a human or animal body or an opening of a pipe in industrial applications. The shaft may have an outer diameter, for example, in the range of 4 mm to 10 mm. The shaft may comprise one or more channels for irrigation and/or through which working instruments may pass (generally referred to as "working channels") in order to achieve a desired effect in the cavity or opening. Preferably, at its distal end, the shaft comprises an electronic image sensor arranged for picking up an image of an object field, whereby the image is generated by an objective lens system. The objective lens system can be arranged at or in a distal end section of the shaft, such that the image is captured on an image sensing surface of the image sensor. The electronic image sensor may be, for example, a charge-coupled device (CCD) or a complementary metal-oxide semiconductor (CMOS). Preferably, the image sensor is configured to convert the captured image into an electrical image signal. The electronic image sensor, preferably arranged in the distal end section of the shaft, transmits the electrical image signals to the proximal end of the shaft by electric lines, such as wires and/or a flexible printed circuit board to the second connector element and further to the first connector element of the handle.

Alternatively, the image sensor may also be positioned in the proximal end section of the shaft and image light collected by the objective lens system may propagate from the distal end section of the shaft to the proximal end section, where the image sensor picks up the image transferred. In this alternative, the shaft comprises a suitable optical image transmission system including, for example, rod lenses for transferring the image light from the distal end section of the shaft to the proximally located image sensor.

A "detachable, rotatable electrical and/or mechanical connection" particularly means that the shaft and the handle can be separated and disconnected from each other by the user, but the shaft and the interface portion of the handle are rotatably fixed together with the same rotation speed and/or same rotational direction during use. In particular, the shaft can be detached from the interface portion and thereby the handle, preferably without use of any tool and, more preferably, easily by hand by the user before, during or after an endoscopic intervention or examination.

The detachable, rotatable electrical and/or mechanical coupling point between the handle and the associated shaft is in particular provided by connecting the "second connector element" of the shaft to the "first connector element" of the interface portion of the handle. The first connector element and the second connector element are in particular part of a plug and socket connection, wherein, preferably, the second connector element is located at the proximal end section or the proximal end of the shaft and the first connector element is arranged at the distal end section or the distal end of the interface portion.

In particular, the "first connector element" by the handle and the "second connector element" by the shaft are formed as corresponding counterparts. Especially, the first connector element and the second connector element are each formed in such a manner, that both parts together provide a form-locking connection. For example, the second connector element can be formed as plug and/or male connector and the first connector element can be formed as socket and/or female connector or vice versa. The first connector element and the second connector element are preferably arranged to be able for a bidirectional transmission. The first connector element or the second connector element as the plug part of the connection, for example, can be a 21-pin plug or a pad plug. Preferably, the distal end and/or the second connector element of the shaft are hermetically sealed in the shaft, so that the shaft is autoclavable and can be sterilized completely by disinfection liquids. Therefore, the proximal end and/or the second connector element can be cast by glass and/or metal within the shaft. In particular, the first and second connector elements are configured for electrically connecting the electrical connection assembly, and there with the stationary electric and/or electronic component of the handle, with the image sensor arranged in the shaft.

The coupling point formed by the first connector element and the second connector element preferably enables a non-rotatable connection of the shaft to the interface portion of the handle during use. Consequently, the shaft is rotatable only in conjunction with the interface portion with respect to the housing and therefore rotatable around the rotational axis of the interface portion relative to the housing. Preferably, the shaft is connectable via the coupling point to the interface portion in such a manner, that a longitudinal axis of the shaft is substantially aligned with the rotational axis of the interface portion, so that the shaft is rotatable around its longitudinal axis together with the interface portion relative to and therefore independent from the orientation of the housing of the handle. Alternatively, the shaft may be configured, and the second connector element located such that the longitudinal axis of the shaft forms an angle to the rotational axis of the interface portion.

An "electrical connection assembly" is an electric component for enabling an electric connection between the first connector element or an intermediate transmission element of the interface portion and a stationary electric and/or electronic component. The electrical connection assembly comprises at least one electric component and/or several electric components. The electrical connection assembly is configured for transmission of the electric image signals from the first connector element of the interface portion to the stationary electronics of the handle and/or for transmitting electric energy and/or control signals from the stationary electronics to the first connector element. In particular, the electrical connection assembly is arranged at the exterior of the interface portion and forms an electrical connection in a multiplicity of rotational positions of the interface portion relative to the housing. Hereby, the electrical connection assembly is configured to maintain the electrical connection in various rotational positions of the interface portion relative to the housing without interruption, in particular completely or at least partially independent from the rotational position or from a corresponding rotation angle of the interface portion.

Preferably, the electrical connection assembly comprises a flexible conductor element providing a flexible and therefore moveable connection between the first connector element and the stationary electric and/or electronic component of the handle. The flexible conductor element, for example, can be a flexible ribbon cable, a flexible elongate circuit board and/or any other flexible electric connection element. Preferably, the flexible conductor element can be twisted around its longitudinal direction and/or can be spooled. Most preferably, the flexible conductor element is configured to be spooled and/or unspooled from the exterior or an outer peripheral surface of the interface portion by rotating the interface portion relative to the housing. Hereby, the rotatability of the electric connection is realized by the spooling and/or unspooling of the flexible conductor element, around and/or at the outside of the interface portion. Hereby, the flexible conductor element can be wrapped around directly on the surface of the interface portion and/or on a respective frame or spool arranged at the outside of the interface portion, when the connected shaft and therewith the interface portion is rotated in one direction. Consequently, the flexible conductor element can be wound off when the shaft and therewith the interface portion is rotated in the opposite direction.

A "rotation" is a circular movement of an object around an axis or point of rotation. A rotation is in particular the circular movement of the interface portion and/or a connected shaft.

A "mechanical rotation stop" is, in particular, a stop which effects, by mechanical means, a stop of the rotation. A mechanical rotation stop is in particular free of a motor and/or a controller.

A "rotation range" is especially the angular range of the rotation. One rotation has a rotation range and therewith angle of 360°.

In a further embodiment of the handle, the mechanical rotation stop comprises a stop piece connected to the housing and a partial groove in an outer peripheral surface of the interface portion or vice versa a stop piece connected to the interface portion and a partial groove in an inner peripheral surface of the housing, wherein the stop piece is engageable with the partial groove.

In a simple design, the mechanical rotation stop is formed by a direct interaction between a stop piece connected to the interface portion or the housing and a partial groove connected to the housing or the interface portion. Hereby, the stop piece runs in the partial groove during rotation until it hits the remaining partitional wall.

Due to the direct interaction of the stop piece and the partial groove each arranged at the housing or the interface portion, a direct and fast stop of the rotation and reliable securing of maintaining the electrical connection assembly are enabled.

Therefore, the user of the video endoscope can hold the handle intuitively in an upright position with a constant orientation while rotating the shaft without concern as to the number of already carried out rotations.

It is especially advantageous that any damage to the electrical connection assembly, e.g. spooled around the interface portion, is prevented by just two elements, the stop piece and the partial groove forming the mechanical rotation stop. Therewith, a simple and robust design of the mechanical rotation stop is provided.

A "stop piece" is a piece or element that stops the rotation of the interface portion and therewith the connected shaft. The stop piece in particular extends into the partial groove and therefore, during rotation, is moved in the partial groove until it hits the partitional wall still existing due to the partial formed groove. The stop piece can be a separate piece and, for example, pluggable to or otherwise connectable to the housing or the interface portion. Alternatively, the stop piece can be permanently connected to the housing or the interface portion.

A "partial groove" is in particular a slot or a trench cut in an outer peripheral surface of the interface portion or in an inner peripheral surface of the housing. In order to leave a partitional wall in the outer peripheral surface of the interface portion or the inner peripheral surface of the housing, the partial groove has, in particular, an angular length of less than 360° in a radial circumferential direction.

For a robust and stable mechanical rotation stop, the stop piece is formed by a nose-piece of the housing or the interface portion.

Therewith, the stop piece is permanently fixed and connected to the housing or the interface portion. Especially the nose-piece is formed as one-piece with the housing or the interface portion. In general, the stop piece and/or nose-piece can be arranged at any position at the housing or interface allowing interaction with the respective groove. For example, in case of a circular form of the inner circumference of the housing or the outer circumference of the interface portion, the stop limit can be located at any angular position between 0° and 360°.

In yet another embodiment of the invention, the partial groove comprises such a length in a radial circumferential direction that at least a rotation of the interface portion in one rotational direction of less than substantially 360° is enabled.

In particular, a rotation of the interface portion in one rotational direction of more than 0° but less than 360° is enabled, and preferably, the range will be as close to 360° as possible, thus approximately 360°. Some embodiments may, for example, enable a rotational range in one rotational direction of approximately 340°.

Therewith, almost one complete rotation is possible, whereby the rotation angle may be limited, in some embodiments, to 340°, the remaining 20° is caused by the dimension of the remaining partitional wall, thus. Self-evidently, hereby the rotation range also depends on the material properties of remaining material in the partial groove. For example, also a complete groove could be used and a strong metal plate with a very small dimension could be inserted in the groove to give a limit stop for the stop piece. Generally, in this design, the rotational range in one direction of the interface portion is given by starting the rotation at the stop piece adjacent to one side of the partitional wall and ends with hitting of the stop piece on the other side of the partitional wall.

For enhancing the rotational range of the interface portion and therewith of a connected shaft, an intermediate ring is arranged freely rotatable between the interface portion and the housing.

An "intermediate ring" is, in particular, a ring which can be inserted between the interface portion and the housing. "Freely rotatable" herein means that the rotation of the ring as such between the interface portion and the housing is not influenced by the interface portion or the housing itself.

In a further embodiment, the intermediate ring comprises a stud with a first end and a second end exceeding in both radial direction over a cross-section area of the intermediate ring and the first end of the stud in engageable with the partial groove of the interface portion or the housing and the second end of the stud is engageable with the stop piece of the housing or the interface portion.

By one end of the stud engageable with the partial groove and the other end of the stud engageable with the stop piece, the range of rotation is enlarged by the intermediate ring further improving the rotatability of the interface portion and therewith a connected shaft and therefore better preventing a tear off of the electrical connection element, especially a flexible circuit board spooled around the interface portion.

A "stud" is especially part of the intermediate ring or an element fixed to the intermediate ring which, in its longitudinal direction, has a higher dimension than the inner and outer diameter of the intermediate ring, meaning the stud extends with both ends over the outer and inner diameter of the intermediate ring and therefore over the material thickness of the intermediate ring. Preferably, the stud is arranged substantially perpendicular to the cross-section area of the intermediate ring. A stud can also be a screw. The stud can have a constant diameter, e. g. as a pin, or a conical or other shape.

For enlarging the rotational range available for the user by using the handle and for improved prevention in tearing off of the electrical connection assembly, a partitional wall of the outer peripheral surface of the interface portion or the inner peripheral surface of the housing, that is free of the partial groove, is a rotatory engaging piece for the first end or the second end of the stud such, that at least a rotation of the interface portion in one rotational direction of greater than 360° and less than 720° is enabled.

Therewith, almost two complete rotations of the interface portion and/or a connected shaft is possible in one rotational direction, meaning either clockwise or counterclockwise, wherein preferably at least a rotation range of substantially up to 690° is enabled.

For example, in case the partitional wall of the partial groove is adjacent to the right side of the lower end of the stud, the partitional wall is rotatable in the clockwise direction until it hits the left side of the lower end of the stud and, afterwards, due to the freely rotatable intermediate ring and the partitional wall as rotatory engaging piece, the intermediate ring rotates likewise in the clockwise direction until the upper end of the stud hits the nose-piece of the housing.

Likewise, it is obvious here, that the range of rotation is only substantial 690° and can be even less or more, depending on the dimension of the stop piece/nose-piece and the stud in the radial circumferential direction and therewith along the groove. Yet in this embodiment, a greater rotation freedom is provided and an almost two-times rotation of the interface portion and therefore the mechanical electrical coupling point between the shaft and the handle is possible. Consequently, this design mimics the operation of a traditional proximal sensor endoscope even better.

In another aspect of the invention, the problem is solved by a video endoscope, in particular medical or industrial video endoscope, comprising a light source and an elongate shaft, wherein the elongate shaft comprises at least one electronic image sensor, a second connector element at the proximal end section of the shaft, which is electrically connected to the at least one electronic image sensor and is detachably connected to a handle, wherein the handle is a handle as described above, so that the first connector element of the interface portion of the handle and the second connector element of the shaft form a detachable electrical and/or mechanical connection and that a rotation range of the shaft connected to the interface portion is limited.

Therewith, a rotatable and connectable video endoscope is provided with two separate system borders consisting of the video endoscope shaft and the handle, which can be flexibly mounted and adapted by the user and, most of all, used intuitively without paying attention to the number of already carried out rotations of the shaft. As the mechanical rotation stop directly and immediately indicates to the user that the user has to change into the other rotational direction to achieve the required object field, overwinding and, consequently, twisting and tearing off the electrical connection assembly is not possible with this video endoscope.

For a fast and correct electrical contacting of the first connector element of the interface portion and the second connector element of the shaft, the first connector element comprises a groove and the second connector element comprises a pin or vice versa for forming a form-closed, detachable mechanical pin-groove-connection in such a manner, that a safe and correct contacting of the first connector element and the second connector element is achieved.

Thus, by forming the form-closed, detachable mechanical pin-groove-connection between the first connector element and the second connector element during connecting both, also the electrical connection between the first connector element and the second connector element is protected and therefore the aligned rotation of both elements is secured. Consequently, a smooth and interruption-free rotation of the shaft connected to the interface portion of the handle is realized, preventing a damage and tearing off of the electrical connection assembly.

For providing the pin-groove-connection, the pin can be arranged at the first connector element and the groove at the second connector element or reciprocal.

A "groove" of the pin-groove-connection is, in particular, a slot or a trench cut into the first connector element or the second connector element. The groove is especially arranged at the outside, face side and/or inside of the first connector element or the second connector element.

A "pin" is an element for fastening and connecting the first connector element and the second connector element. A pin is, in particular, a rigid and/or inflexible material meant to be inserted in the groove. A pin can be a straight or a push pin. A pin can also be spring loaded. Likewise, the movement of the pin can be restricted by the form of the groove and/or the pin and the groove may form a form-closed connection.

In a further embodiment of the video endoscope, the pin-groove-connection is configured such, that the pin-groove-connection is an engaging piece for the rotation of the shaft and the interface portion.

By the pin-groove-connection, rotational forces due to the handling of and therewith the rotation of the shaft by the user are better transmitted to the interface portion via the first connector element and the second connector element and also variating rotational forces can be absorbed by the pin-groove-connection giving a smooth rotation of the shaft and the interface portion.

Consequently, the electric contacts, such as pins of a 21-pin plug, do not bear the forces and, therefore, the mechanical strain on the electrical connection of the first connector element and the second connector element is decreased.

In a further embodiment, for an optimal rotational coupling, the pin is arranged at a proximal end section of the second connector element, in particular at an outer surface, a proximal face side and/or in the second connector element, and/or the groove is arranged at a distal end section of the first connector element, in particular along an outer surface, at a distal face side and/or in the first connector element.

In a further embodiment, the groove is arranged at a proximal end section of the second connector element, in particular along an outer surface, at a proximal face side and/or in the second connector element, and/or the pin is arranged at a distal end section of the first connector element, in particular at an outer surface, at a distal face side and/or in the first connector element.

For facilitating the user-friendly coupling of the shaft and the handle, the pin is wedge-shaped and an opening of the groove is wide-mouthed.

For strengthening the mechanical connection and ensuring a reliable electric connection between the first and second connector element, one of any number of mechanical coupling mechanisms known in the art may be provided. Such mechanical coupling mechanisms include a quarter turn coupling, a quick connect coupling, a ball and groove coupling, etc. The coupling mechanisms generally consist of a grasping mechanism located on either the elongate shaft or the handle, and a corresponding holding mechanism located on the other of the handle or elongate. In a preferred embodiment, the elongate shaft comprises an eyepiece cup, acting as the holding mechanism, and the handle comprises a claw coupling, acting as the grasping mechanism, thereby, in a connected state, the elongate shaft and the handle are further mechanically coupled by the eyepiece cup and the claw coupling to provide greater stability and protection against accidental disconnection.

Therewith, the eyepiece cup on the shaft serves in combination with the claw coupling on the handle as a mechanical safeguard and/or lock for the electrical connection of both parts.

In the connected state, the coupling plate and/or the eyepiece cup is pressed by the claw and therewith the complete shaft against the interface portion. By this mechanical claw coupling, an additional mechanical connection with a greater connecting surface than the first and the second connector elements is provided. Consequently, the shaft is additionally secured at the housing and/or interface portion of the handle.

A "claw coupling", also called dock-clutch, is in particular a clutch that couples two components, whereby at least one or both components are rotatable, by interference or clearance fit. Preferably, the claw of the claw coupling is designed such that the coupling plate and/or the eyepiece cup is pushed towards the interface portion, while both the shaft with the coupling plate and/or eyepiece cup and the interface portion are rotating at the same speed without slip.

In yet another embodiment of the video endo scope, the light source is a cold-light source or an LED, wherein the cold-light source is arranged in a proximal end section of the shaft or at a proximal end of the handle or the LED is arranged in a proximal end section of the shaft or in the handle.

Besides using two different kinds of light sources, such as a cold-light source or an LED, also the respective light source can be arranged in different locations within the video endoscope. In case of connected cold-light source the connection of the cold-light source can be located distally in the video endoscope, for example after the second connector element further to the distal end of the shaft. Alternatively, a proximal cold light source is used, which can be connected to the proximal end of the handle, wherein the light is transmitted by respective optic elements through the coupling point until the distal end of the shaft.

In case of an integrated LED, the LED likewise can be arranged distally of the video endoscope and, therewith, after the second connector element towards the distal end of the shaft. Alternatively, the LED can be proximally arranged in the handle. Therewith, a detachable, rotatable mechanical, electrical and/or optical connection between the shaft and the handle is provided, wherein the kind of light source as well as its arrangement can be freely chosen and a reliable electrical connection between the shaft and the handle is still ensured.

A "cold-light" source is a light source which, in particular, emits light with a greatly reduced infrared component. A cold-light source is especially used for a very highly intensive light required in the visible spectral range, but where a heat development of an ordinary light source would be disruptive or even harmful. A cold-light source comprises a halogen or xenon lamp and a rotational elliptical reflector.

An "LED" ("Light-Emitting Diode") is a semiconductor light source that emits light when current flows through it. In particular, electrons in the semiconductor combine with the electron holes, releasing energy in the form of photons.

In a further embodiment, the handle is arranged coaxial, angular and/or movable relative to the shaft.

Therewith, the arrangement of the handle itself can be chosen, adapted and/or moved relative to the shaft, while still maintaining a reliable electrical and mechanical connection between the handle and the rotatable shaft.

The invention is further explained by the following exemplary description of particular embodiments.

BRIEF DESCRIPTION OF THE FIGURES

FIG. 9 is a three-dimensional, cross-sectional view of an embodiment of the handle with a single mechanical rotation limit.

FIG. 10 is a cross-sectional view of the single mechanical rotation limit.

DETAILED DESCRIPTION OF THE INVENTION

Figure 1:
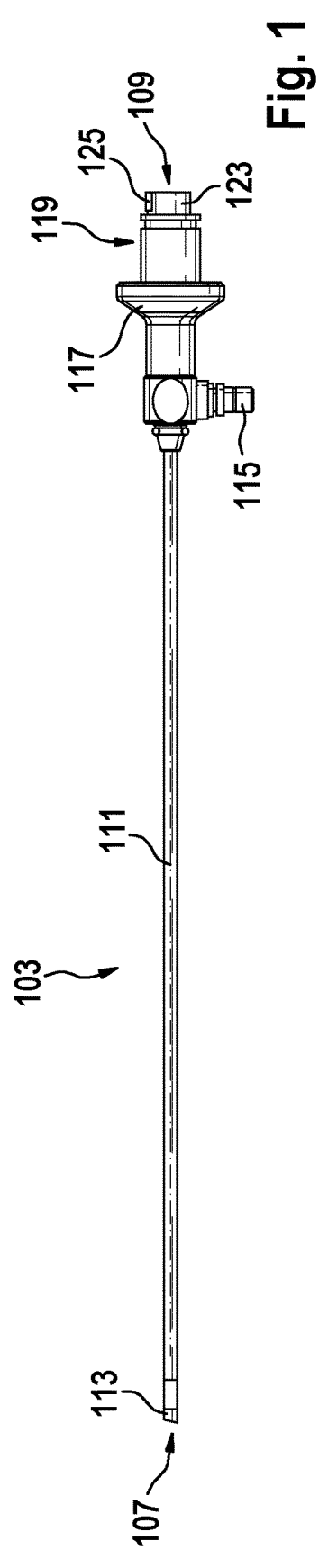
FIG. 1 is a three-dimensional view of a shaft of a video endoscope.
Figure 2:
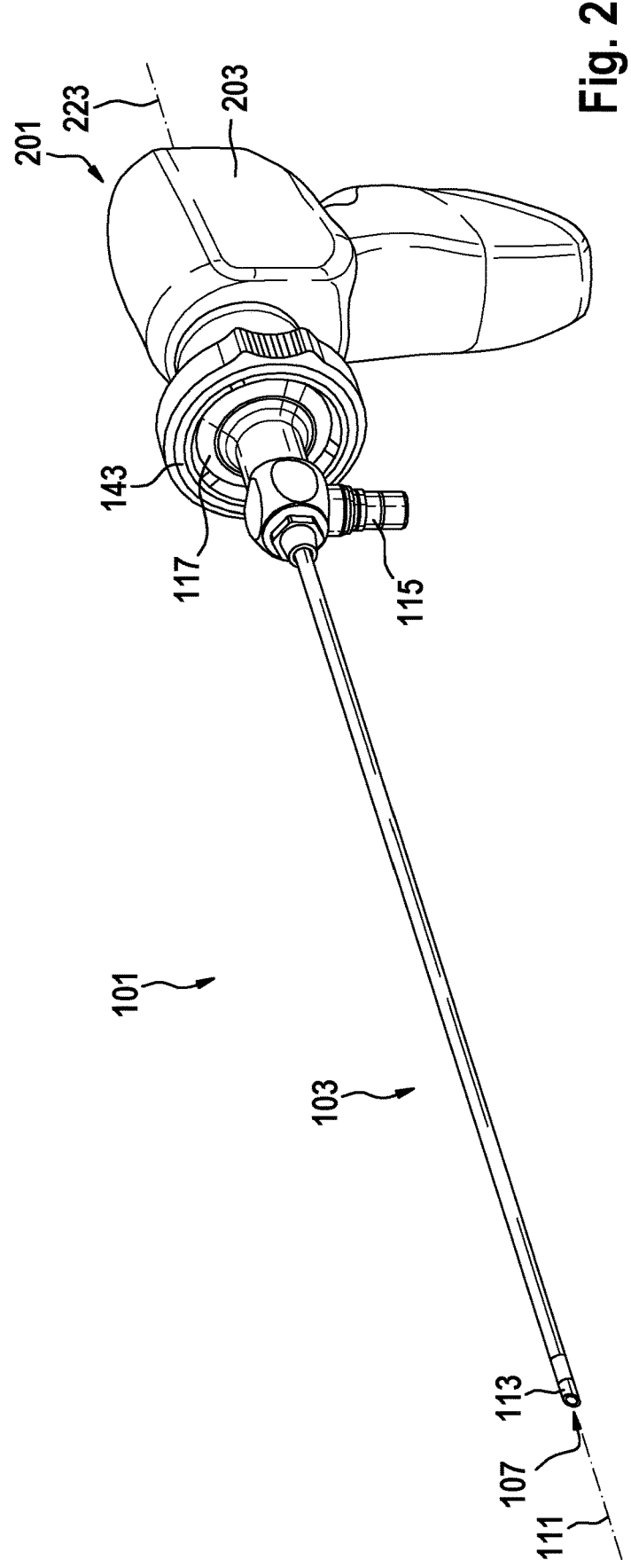
FIG. 2 shows a three-dimensional view on the shaft and a handle of the video endoscope from the distal end.
Figure 3:
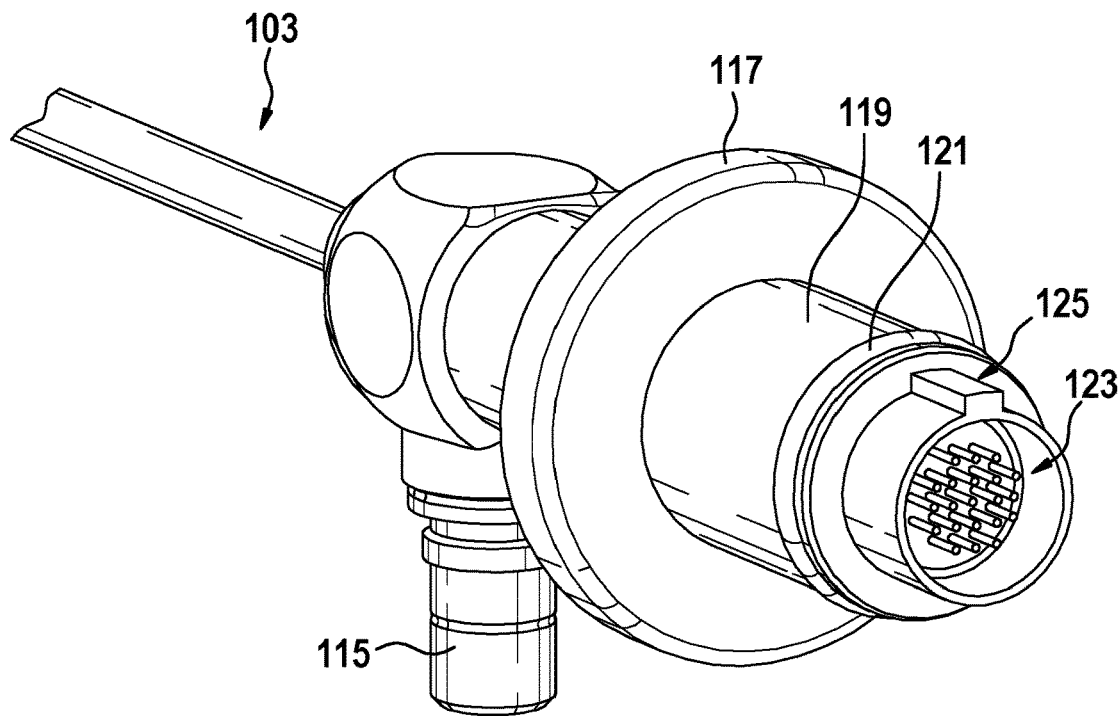
FIG. 3 is a three-dimensional view on the proximal end of the shaft with the second connector element.

A video endoscope 101 comprises a shaft 103 and a handle 201 (see FIG. 2). The shaft 103 comprises at its distal end 107 two image sensors 113. Furthermore, the shaft 103 comprises a longitudinal axis 111 between its distal end 107 and its proximal end 109. At its proximal end 109, the shaft 103 comprises a second connector element 119 with a 21-pin plug 123. The 21-pin plug 123 has a pin 125 at its top side (see FIG. 3). The 21-pin plug 123 is arranged hermetically sealed to the second connector element 119. Furthermore, the second connector element 119 comprises an O-ring seal 121 around its outer peripheral surface for sealing a connection with a first connector element 213. Furthermore, the shaft 103 comprises an eyepiece cup 117 and a light post 115 for connecting a light source.

Figure 4:
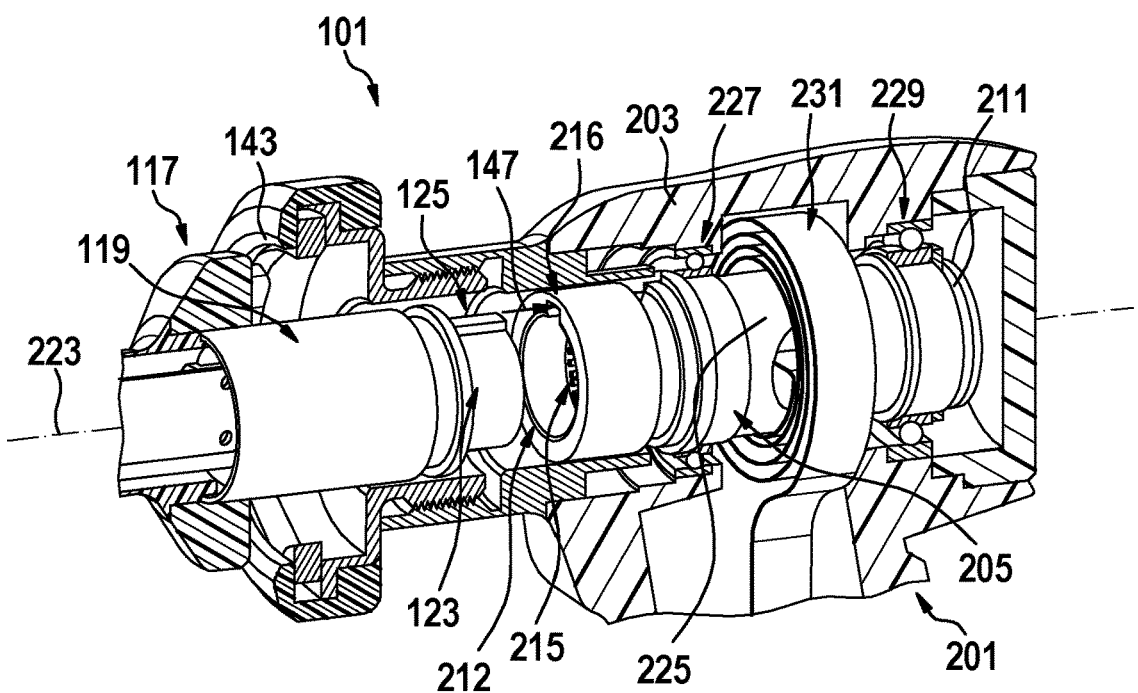
FIG. 4 is a three-dimensional, cross-sectional view of the second connector element of the shaft with a 21-pin plug in a still detached state and an interface portion of the handle.

In a connected state, the shaft 103 and the handle 201 form the video endoscope 101. Hereby, the eyepiece cup 117 of the shaft 103 is an additionally, mechanically connected via a claw coupling 143 of the handle 201. The longitudinal axis 111 of the shaft 103 falls together with a rotation axis 223 of an interface portion 205 of the handle 201. The second connector element 119 of the shaft 103 is connected via the 21-pin plug 123 to a socket 215 of the interface portion 205. Hereby, the second connector element 119 together with the shaft 103 is moved in a coupling direction 147 (see FIG. 4), wherein the pin 125 and the corresponding groove 217 facilitate the easy connection of the shaft 103 via the second connector element 119 with the interface portion 205 of the handle 201 and the correct alignment of the pins of the 21-pin plug 123 in the socket 215.

The interface portion 205 is supported within a housing 203 of the handle 201 by a first ball bearing 227 and a second ball bearing 229. The first ball bearing 227 is arranged between a distal end 212 of the interface portion 205 and a flexible circuit board 231, wherein the flexible circuit board 231 is wrapped around an outer peripheral surface 225 of the cylindric interface portion 205 and is arranged between the first ball bearing 227 and the second ball bearing 229. The second ball bearing 229 is arranged at the proximal end 211 of the interface portion 205.

Figure 5:
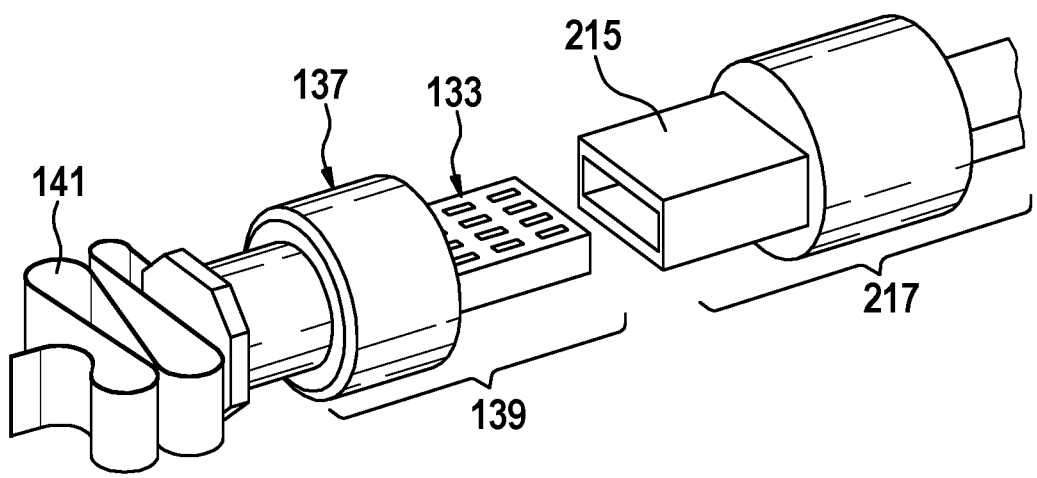
FIG. 5 is a three-dimensional view of a male connector with a pad plug.
Figure 6:
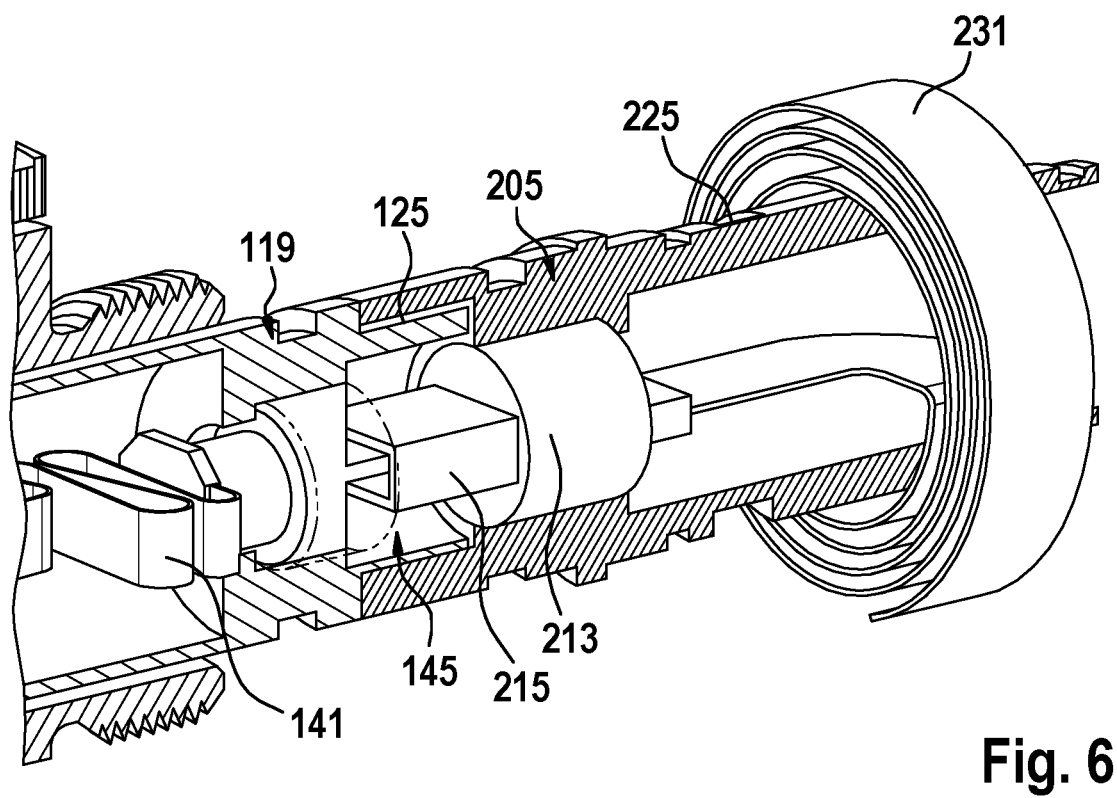
FIG. 6 is a three-dimensional view of the male connector in a second connector element connected to a first connector element of an interface portion.

In an alternative, instead of a 21-pin plug 123, a male connector 139 consisting of a bush 137 and a pad plug 133 is used (FIGS. 5 and 6). The male connector 139 is connected via a flexible cable 141 along the longitudinal axis 111 with the image sensors 113 (not shown). The pad plug 133 has a rectangular form and several electric contacts in form of small pads. The bush 137 includes an autoclavable, tight metal housing. The male connector 139 is hermetically, closely welded with the second connector element 119. The pad plug 133 of the male connector 139 fits into a socket 215 of a corresponding female connector 217, which is included in the first connector element 213 of the interface portion 205 of the handle 201. The female connector 217 of the first connector element 213 is directly connected with a flexible circuit board 231, which is spooled around the peripheral surface 225 of the interface portion 205.

For connecting the shaft 103 and therewith the second conductor element 119 to the first connector element 213 of the interface portion 205 of the handle 201, the shaft 203 and the second connector element 119 are moved towards the proximal end of the handle 201, whereby the pad plug 133 is inserted in the socket 215 of the female connector 217 of the first connector element 213. Hereby, likewise, the connection is facilitated by a pin 225 arranged in the second connector element 119 which is inserted in a corresponding, non-shown groove in FIG. 6 of the first connector element 213.

Figure 7:
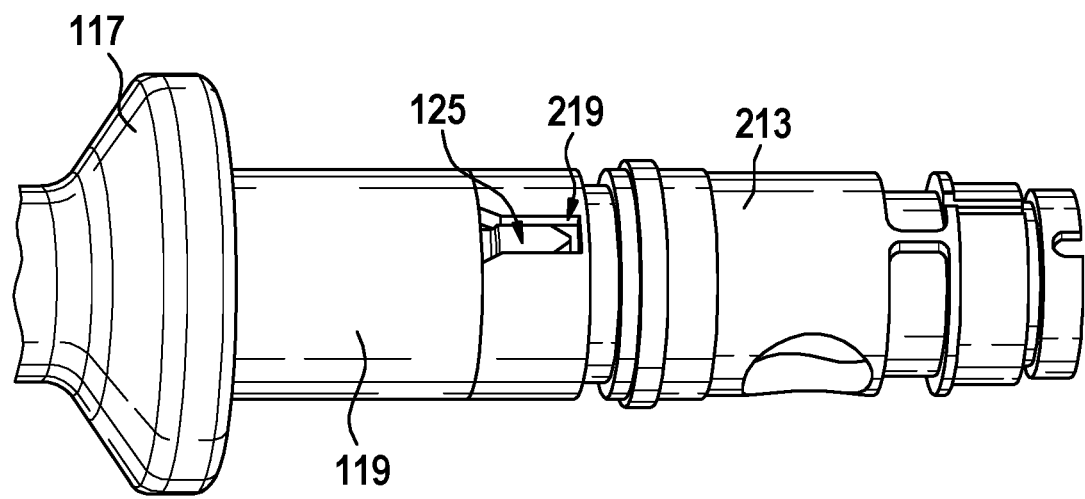
FIG. 7 is a three-dimensional view on a pin-groove-connection of a first connector element and a second connector element in the connected state.
Figure 8:
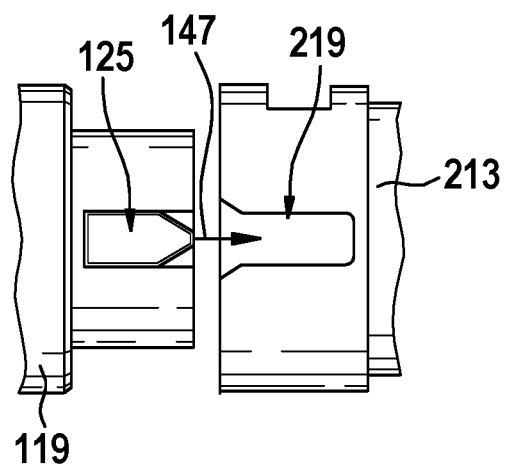
FIG. 8 is a three-dimensional view on the second connector element with a pin and a first connector element with a tapered groove in the detached state.

Additionally, the connection between the second conductor element 119 and the first connector element 213 can be mechanically strengthened by a wedge-shaped pin 225 arranged at the second connector element 119 and a corresponding tapered groove 219 arranged at the outer surface of the first connector element 213, correspondingly (see FIG. 8 in the detached state and FIG. 7 in the connected state). By this pin-groove-connection, a user-friendly coupling of the shaft 103 and the interface portion 205 of the handle 201 is enabled, wherein this pin-groove-connection stabilizes the smooth, common rotation of the shaft 103 and the interface portion 205.

In another alternative of the handle 201, the housing 203 and the interface portion 205 form a single mechanical rotation limit 241. The housing 203 comprises a nose-piece 243, which reaches into a partial groove 245 of the interface portion 205. As the partial groove 245 is not cut completely into the circumferential peripheral surface of the interface portion 205, a partitional wall 247 remains at the outer surface of the interface portion 205 (see FIGS. 9 and 10).

In case of the shaft 103 with the second connector element 119 being connected to the electric coupling point 145 of the interface portion 205 (the connected state is not shown in FIG. 9) and a user rotates the shaft 103 in a single rotational direction 251 counterclockwise, the partitional wall 247, which is directly adjacent to the left side of the nose-piece 243 (see FIG. 10), is rotated approximately in a rotation range of 340°, wherein the nose-piece 243 runs in the partial groove 245 until the partitional wall 247 hits the right side of the nose-piece 243 giving a limit stop. By this limit stop formed by the nose-piece 243 and the partial groove 245, the user of the handle 201 and the video endoscope 101 gets the indication that, for adapting a view on the object field, the user has to turn the shaft by hand in the other direction clockwise to prevent a damage of the flexible circuit board 231 spooled around the outer peripheral surface 225 of the interface portion 205.

Figure 11:
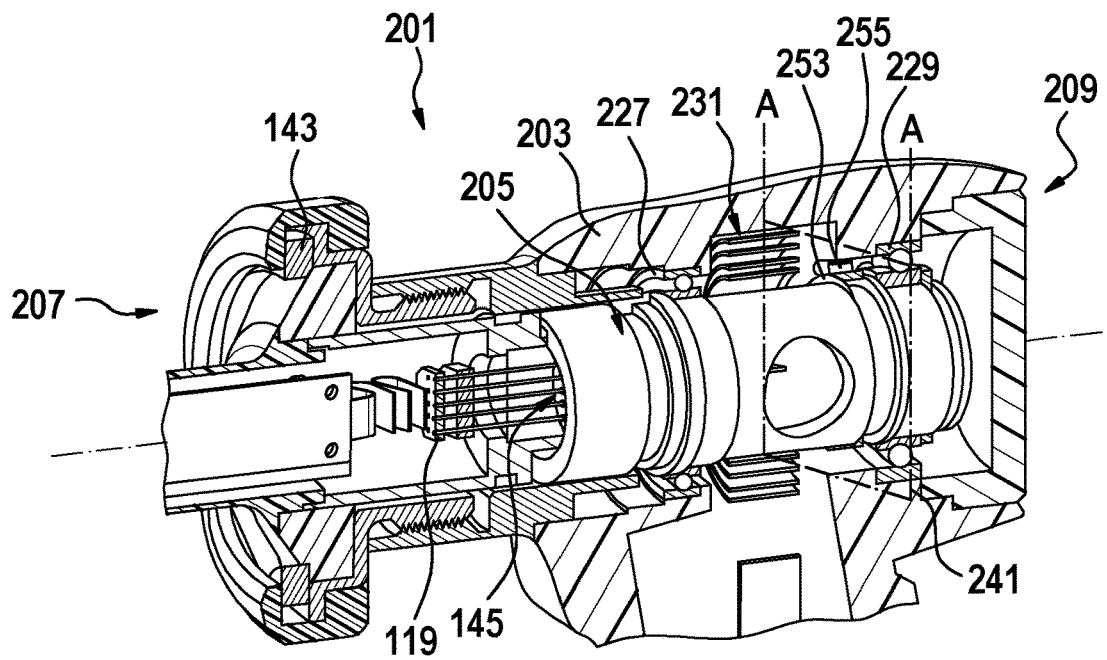
FIG. 11 is a three-dimensional sectional view of another embodiment of the handle connected with a first connector element with a double mechanical rotation limit.
Figure 12:
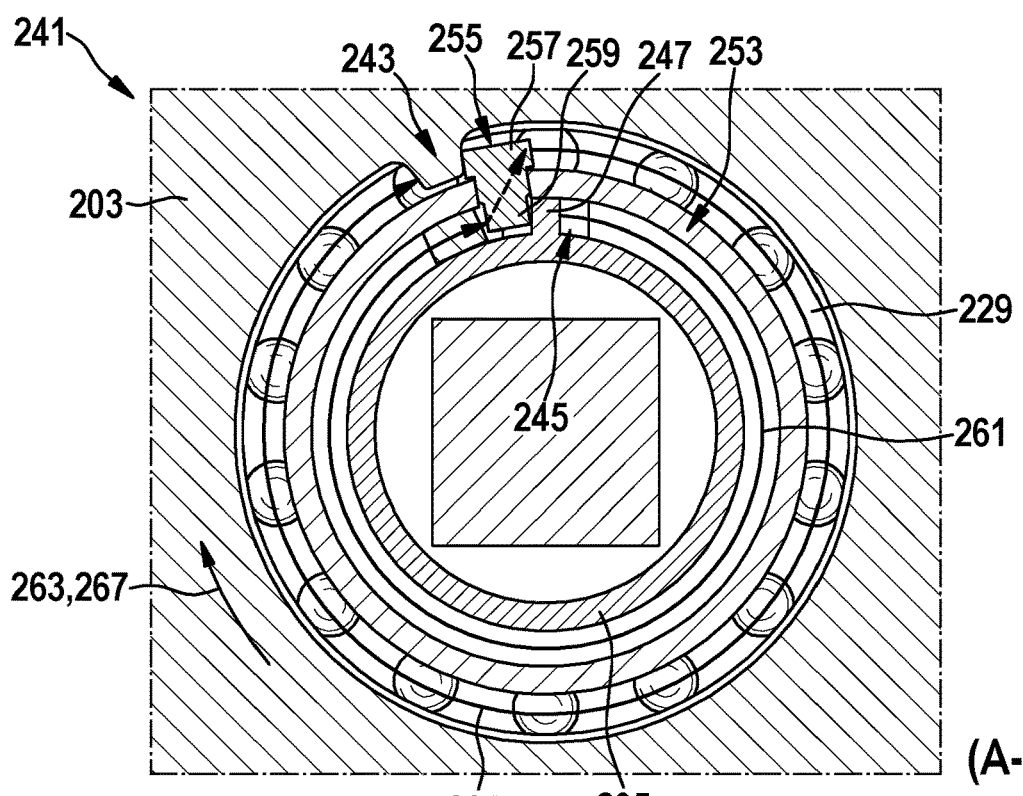
FIG. 12 is a cross-sectional view of the double mechanical rotation limit.

In another alternative of the handle 201, which comprises the components as described above and is shown in the connected state in FIG. 11, an additional intermediate ring 253 is arranged between the housing 203 of the handle 201 and the interface portion 205, by which a double mechanical rotation limit 241 is formed. In FIG. 12, the cross-sectional view on the double mechanical rotation limit 241 is shown from the distal end 207 of the handle 201 towards the proximal end of the handle 209 (compare FIG. 11), so that the second ball bearing 229 is arranged behind the intermediate ring 253. The intermediate ring 253 comprises a stud 255 with an outer end 257 and an inner end 259 of the stud 255. Hereby, the outer end 257 and the inner end 259 extend over a cross-section area of the intermediate ring 253 in both radial directions. Hereby, the outer end 257 is engageable with the nose-piece 243 of the housing 203 and the inner end 259 of the stud 255 is engageable with the partial groove 245 and, respectively, with the partitional wall 247 of the interface portion 205. Therewith, the freely rotatable intermediate ring 253 is positioned by the stud 255 between the housing 203 and the interface portion 205.

In case the user of the video endoscope 101 rotates the shaft 103 in the clockwise first rotational direction 263, the intermediate ring 253 with the stud 255 stays at its initial position, while the partitional wall 247, due to the rotation, moves in the first rotational direction 263, leaving the right side of the inner end 259 of the stud 255 along a first rotation range 261 of approximately 340° given by the partial groove 245 until the right side of the side partitional wall 247 hits the left side of the inner end 259 of the stud 255. By the simultaneous respective movement of the partial groove 245, the inner end 259 of the stud 255 is now, likewise, itself enabled to rotate within the partial groove 245 along a second rotational range 265 in a second rotational direction 267 until it hits the left side of the nose-piece 243 of the housing 203, wherein the first and second rotational directions 263 and 267 have the same direction. Consequently, after a first rotational range 261 of approximately 340°, the partitional wall 247 is a rotatory engaging piece for the inner end 259 of the stud 255 and therewith, by rotating the shaft 103 and the connected interface portion 205, a second, almost complete rotation is enabled with a rotation range 265, so that, overall, a rotation of approximately 690° is possible before the outer end 257 of the stud 255 hits the nose-piece 243 at the left side of the nose-piece 243 and therewith forms the final limit stop. Therewith, an almost two-times rotation of the rotatable mechanical and electrical coupling point 145 of the shaft 103 and the interface portion 205 of the handle 201 is enabled.

Consequently, a video endoscope 101 is provided with a rotatable and detachable electrical and mechanical connection between the shaft 103 and the interface portion 205 of the handle 201 protecting the flexible circuit board 231 by a rotation limit of the interface portion 205 as well as by a pin-groove-connection and therewith allowing the reliable transmission of image data from the two image sensors 113 in the shaft 103 to the handle 201 and further to an external data processing and displaying unit.

REFERENCE NUMERALS

101 Video endoscope
103 Shaft
107 Distal end of shaft
109 Proximal end of shaft
111 Longitudinal axis
113 Image sensor
115 Light post
117 Eyepiece cup
119 Second connector element
121 Seal
123 21-pin plug
125 Pin
133 Pad plug
135 Metal Housing
137 Bush
139 Male connector
141 Flexible cable
143 Claw coupling
145 Electric coupling point
147 Coupling direction
201 Handle
203 Housing
205 Interface portion
207 Distal end of handle
209 Proximal end of handle
211 Proximal end of interface portion
212 Distal end of interface portion
213 First connector element
215 Socket
216 Corresponding groove (to pin 125)
217 Female connector
219 Tapered groove
221 Flexible cable
223 Rotation axis
225 Peripheral surface
227 First ball bearing
229 Second ball bearing
231 Flexible circuit board
241 Mechanical rotation limit
243 Nose-piece of housing
245 Partial groove
247 Partitional wall of interface portion
249 Single rotation range
251 Single rotational direction
253 Intermediate ring
255 Stud
257 Outer end
259 Inner end
261 First rotation range
263 First rotational direction
265 Second rotation range
267 Second rotational direction

The invention claimed is:

1. A handle for a video endoscope, comprising
a housing;
an interface portion;
an electrical connection assembly; and
a mechanical rotation stop,
wherein the interface portion is rotatably supported relative to the housing, and wherein the interface portion comprises a first connector element at its distal end section, the first connector element being connectable to a second connector element of an associated elongate shaft of the video endoscope to form a detachable, rotatable electrical and mechanical connection between the handle and the associated shaft, and wherein the electrical connection assembly is
at least partially wrapped around an exterior of the interface portion forming an electrical connection to the handle, wherein the first connector element is electrically connected to the electrical connection assembly, and
wherein the mechanical rotation stop limits a rotation of the interface portion relative to the housing, such that a rotation range of the interface portion and/or the connected shaft is limited and thereby damage to the electrical connection assembly is prevented.

2. The handle of claim 1 wherein the mechanical rotation stop comprises a stop piece connected to the housing and a partial groove in an outer peripheral surface of the interface portion, or vice versa a stop piece connected to the interface portion and a partial groove in an inner peripheral surface of the housing, wherein the stop piece is engageable with the partial groove.

3. The handle of claim 2 wherein the stop piece is formed by a nose-piece of the housing or the interface portion.

4. The handle of claim 3 wherein the partial groove comprises a length in a radial circumferential direction enabling a rotation of the interface portion in one rotation direction of greater than approximately 340° and less than approximately 360°.

5. The handle of claim 4 wherein an intermediate ring is arranged freely rotatable between the interface portion and the housing.

6. The handle of claim 5 wherein the intermediate ring comprises a stud with a first end and a second end exceeding in both radial directions over a cross section area of the intermediate ring and the first end of the stud is engageable with the partial groove of the interface portion or the housing and the second end of the stud is engageable with the stop piece of the housing or the interface portion.

7. The handle of claim 6 wherein a partitional wall of the outer peripheral surface of the interface portion or of the inner peripheral surface of the housing, that is free of the partial groove, is a rotatory engaging piece for the first end or second end of the stud such, that at least a rotation of the interface portion in one rotational direction of greater than 360° and less than 720° is enabled.

8. The handle of claim 2 wherein an intermediate ring is arranged freely rotatable between the interface portion and the housing.

9. The handle of claim 8 wherein the intermediate ring comprises a stud with a first end and a second end exceeding in both radial directions over a cross section area of the intermediate ring and the first end of the stud is engageable with the partial groove of the interface portion or the housing and the second end of the stud is engageable with the stop piece of the housing or the interface portion.

10. The handle of claim 2 wherein a partitional wall of the outer peripheral surface of the interface portion or of the inner peripheral surface of the housing, that is free of the partial groove, is a rotatory engaging piece for the first end or second end of the stud such, that at least a rotation of the interface portion in one rotational direction of greater than 360° and less than 720° is enabled.

* * * * *